(12) United States Patent
Okada et al.

(10) Patent No.: US 7,056,476 B2
(45) Date of Patent: Jun. 6, 2006

(54) REFRIGERATOR AND DEODORIZER PRODUCING OZONE BY HIGH-VOLTAGE DISCHARGE

(75) Inventors: Daishin Okada, Kameoka (JP); Noboru Segawa, Yokohama (JP); Naohiko Shimura, Atsugi (JP); Takeshi Imamura, Yokohama (JP); Takao Hattori, Ibaraki (JP); Takumi Oikawa, Ibaraki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 677 days.

(21) Appl. No.: 09/973,929

(22) Filed: Oct. 11, 2001

(65) Prior Publication Data
US 2002/0037240 A1 Mar. 28, 2002

(51) Int. Cl.
*A62B 7/08* (2006.01)
*B32B 5/02* (2006.01)

(52) U.S. Cl. ............................. 422/121; 62/78; 62/264; 422/122; 422/123; 422/124

(58) Field of Classification Search ................ 422/121, 422/122, 123, 124, 4, 5, 107; 62/264, 78
See application file for complete search history.

(56) References Cited

U.S. PATENT DOCUMENTS

| | | | | |
|---|---|---|---|---|
| 4,780,277 A | * | 10/1988 | Tanaka et al. | 422/4 |
| 4,904,289 A | * | 2/1990 | Miyakami et al. | 62/157 |
| 4,954,465 A | * | 9/1990 | Kawashima et al. | 502/5 |
| 4,955,208 A | * | 9/1990 | Kawashima et al. | 62/264 |
| 5,078,971 A | * | 1/1992 | Matuda et al. | 422/121 |
| 5,136,170 A | * | 8/1992 | Gellert | 250/492.1 |
| 5,230,220 A | * | 7/1993 | Kang et al. | 62/78 |
| 5,865,959 A | * | 2/1999 | Meinzer et al. | 204/157.3 |
| 6,235,090 B1 | * | 5/2001 | Bernstein et al. | 96/57 |

FOREIGN PATENT DOCUMENTS

| JP | 59012732 | * | 7/1982 |
|---|---|---|---|
| JP | 08-266854 | | 10/1996 |

* cited by examiner

*Primary Examiner*—Krisanne Jastrzab
(74) *Attorney, Agent, or Firm*—Pillsbury Winthrop Shaw Pittman LLP

(57) ABSTRACT

A refrigerator includes a deodorizer disposed in a cold air circulation path for deodorizing an atmosphere in the refrigerator. The deodorizer includes discharging means for producing ozone and ultraviolet rays by means of high-voltage discharge and a photocatalyst module for decomposing an odor component and injurious matter contained in the atmosphere by means of photocatalyst.

14 Claims, 15 Drawing Sheets

REFRIGERATOR AND DEODORIZER PRODUCING OZONE BY HIGH-VOLTAGE DISCHARGE

BACKGROUND OF THE INVENTION

1. Field of the Invention

This invention relates to a refrigerator provided with a deodorizer disposed in a circulation path for cold air so that the circulated cold air is deodorized and further to a deodorizer for deodorizing air by decomposing odor component and/or injurious matter contained in the air.

2. Description of the Related Art

In conventional household refrigerators, a platinum catalyst is disposed near a defrosting heater so that odor component contained in air is adsorbed. The heater is energized in a defrosting operation so that the adsorbed odor component is thermally decomposed, whereby the interior of the refrigerator is deodorized. However, a deodorizer providing a higher deodorizing performance has been required in order that an offensive odor in the refrigerator may be eliminated and may be prevented from scenting other food.

Recent refrigerators have been provided with two evaporators for a cold-storage compartment and a freezing compartment respectively. The humidity in the cold-storage compartment is set to be higher using the two evaporators so that an improvement is achieved in the preservation of freshness of food. However, when the humidity is increased in the cold-storage compartment, odor tends to become stronger and bacteria tend to increase.

In view of the foregoing circumstances, a deodorizer using oxidation of ozone has been equipped in refrigerators. However, odor component cannot sometimes be decomposed completely even by the oxidation of ozone such that intermediate products are produced.

Furthermore, odor component is oxidized by a photocatalyst. For example, this is achieved by irradiating ultraviolet rays onto a photocatalyst material such as titanium oxide. This method can obtain a larger oxidizing force than from ozone. However, a fluorescent lamp is required to irradiate ultraviolet rays onto the photocatalyst material. Since the fluorescent lamp contains mercury, consideration is necessary so that environmental load is not increased when the refrigerator or deodorizer is disposed of. Thus, the deodorizer employing the photocatalyst entails a problem of handling the fluorescent lamp in the case of disposition thereof.

A demand for eliminating odor component and injurious matter contained in the air in a residence has been increased with improvement in residential gastightness and chronicity in contamination of outdoor air. In particular, a demand for eliminating cigarette smoke, metabolic odor or volatile organic compound (VOC) such as formaldehyde contained in building material has been increased. The prior art has provided two major methods of eliminating odor component and injurious matter. In one method, an adsorbent such as activated charcoal is used to eliminate the odor component. In the other method, odor component is caused to react upon drugs so that the nature of the odor component is changed.

In the aforesaid first method, however, the adsorbent has a definite limit in an amount of odor component to be adsorbed. Accordingly, the adsorbent needs to be periodically replaced by a new one. Further, even before the adsorbing performance saturates, the odor component which has been once adsorbed by the adsorbent is released into air again at a final stage of the service life of the adsorbent. In the other method, the drug upon which the odor component is caused to react needs to be supplemented or replaced, resulting in complicatedness in maintenance. Further, control for adjusting the concentration of the drug released into air is difficult.

A catalytic reaction with a high deoxidation potential is required in order that an injurious gas component such as formaldehyde may be eliminated. For example, in decomposition by oxidation with use of ozone, the injurious gas component is only converted into an intermediate product due to decomposition but cannot completely be eliminated for harmlessness. Further, for example, formaldehyde or the like can be decomposed by irradiating ultraviolet rays onto a photocatalyst material such as titanium oxide. Irradiation of ultraviolet rays necessitates a fluorescent lamp. However, the fluorescent lamp contains mercury. Accordingly, a due consideration is necessary for adverse effect on environment when the fluorescent lamp is disposed of. Thus, conventional deodorizers using the fluorescent lamp entail a problem of dealing for disposition.

SUMMARY OF THE INVENTION

Therefore, an object of the present invention is to provide a refrigerator with a deodorizer which can achieve an improved deodorizing function and which requires no special handling when disposed of.

Another object of the invention is to provide a deodorizer which can eliminate injurious gas components etc. without requiring supplementation or replacement of drug and any special dealing for disposition.

The present invention provides a refrigerator in which a deodorizer is provided in a cold air circulation path for deodorizing an atmosphere in the refrigerator, the refrigerator further comprising a heat exchanger having a cold air inlet, the deodorizer comprising discharging means having a plurality of wire-shaped discharge electrodes disposed across the cold air circulation path and a flat counter electrode, the discharging means producing azone and ultraviolet rays by means of high-voltage discharge, the counter electrode having a number of slits formed therethrough so that cold air for refrigeration flows through the slits, the slits being arranged so that the cold air flows therethrough across the counter electrode, a photocatalyst module provided between the discharge electrodes and the counter electrode for decomposing an odor component and injurious matter contained in the atmosphere by means of photocatalyst, and zone decomposing means for decomposing the zone produced by the discharging means, the ozone decomposing means being disposed at a downstream side of at least the discharging and the photocatalyst module with respect to a direction in which the cold air flows and further in the cold air inlet of the heat exchanger.

According to the above-described construction, the ultraviolet rays are produced by the high-voltage discharge of the discharging means. Further, when subjected to the ultraviolet rays, the photocatalyst module performs a photocatalytic reaction. As a result, the odor component contained in the circulated cold air is decomposed by oxidation to thereby be eliminated. Thus no special handling is required in the case of disposition of the refrigerator or the deodorizer since the ultraviolet rays can be produced without using a fluorescent lamp.

Furthermore, ozone is also produced by the high-voltage discharge. Accordingly, the odor component in the refrigerator is further decomposed by the oxidation of the ozone. Additionally, the produced ozone is diffused into the interior of the refrigerator with the circulated cold air such that an ozonic atmosphere is formed. Since the ozonic atmosphere provides an antibacterial action for food stored in the refrigerator, the freshness of the food can be maintained.

Furthermore, the ozone produced by the high voltage discharge is decomposed by the ozone decomposing means in the aforesaid construction. Consequently, the ozonic concentration can be prevented from an excessive increase and accordingly, the user can be prevented from having a smell of ozone when opening the door of the refrigerator. Further, since decomposition of ozone tends to produce more active oxygen, oxidation can further be facilitated and the deodorizing efficiency can further be improved.

Furthermore, when ozone produced by the deodorizer is circulated so as to pass through an evaporator, there is a possibility that the evaporator and piping may adversely be affected. When the ozone decomposing means is disposed in the cold air inlet of the heat exchanger in view of the aforesaid problem, ozone is decomposed before the circulated cold air is taken into the heat exchanger. Consequently, inner components of the refrigerator can be prevented from being adversely affected by the ozone.

In further another preferred form, the refrigerator further comprises control means for controlling the deodorizer so that the discharging means discharges electricity when cold air is circulated in the refrigerator. Upon circulation of cold air, the cold air containing an odor component is caused to flow into the deodorizer so that the cold air is deodorized. Consequently, the deodorization can be performed more efficiently.

In further another preferred form, the discharging means includes two electrodes and the photocatalyst module is disposed between the electrodes of the discharging means. Since the ozone produced by the discharging means is efficiently irradiated onto the photocatalyst module, the photocatalytic reaction can be facilitated.

The refrigerator preferably further comprises a refrigerator body and the deodorizer is attached to and detached from the refrigerator body. When the deodorizer is detached from the refrigerator body, substances resulting from decomposition and adherent to portions of the deodorizer can easily be removed.

At least the discharging means of the deodorizer is preferably powered by a battery. Since the deodorizer is completely discrete from the refrigerator, the deodorizer can be disposed at any position in the refrigerator. Additionally, the deodorizer in accordance with the invention can be provided in a refrigerator which does not have a deodorizing function.

BRIEF DESCRIPTION OF THE DRAWINGS

Other objects, features and advantages of the present invention will become clear upon reviewing the following description of preferred embodiments, made with reference to the accompanying drawings, in which.

DETAILED DESCRIPTION OF EMBODIMENTS

Figure 1:
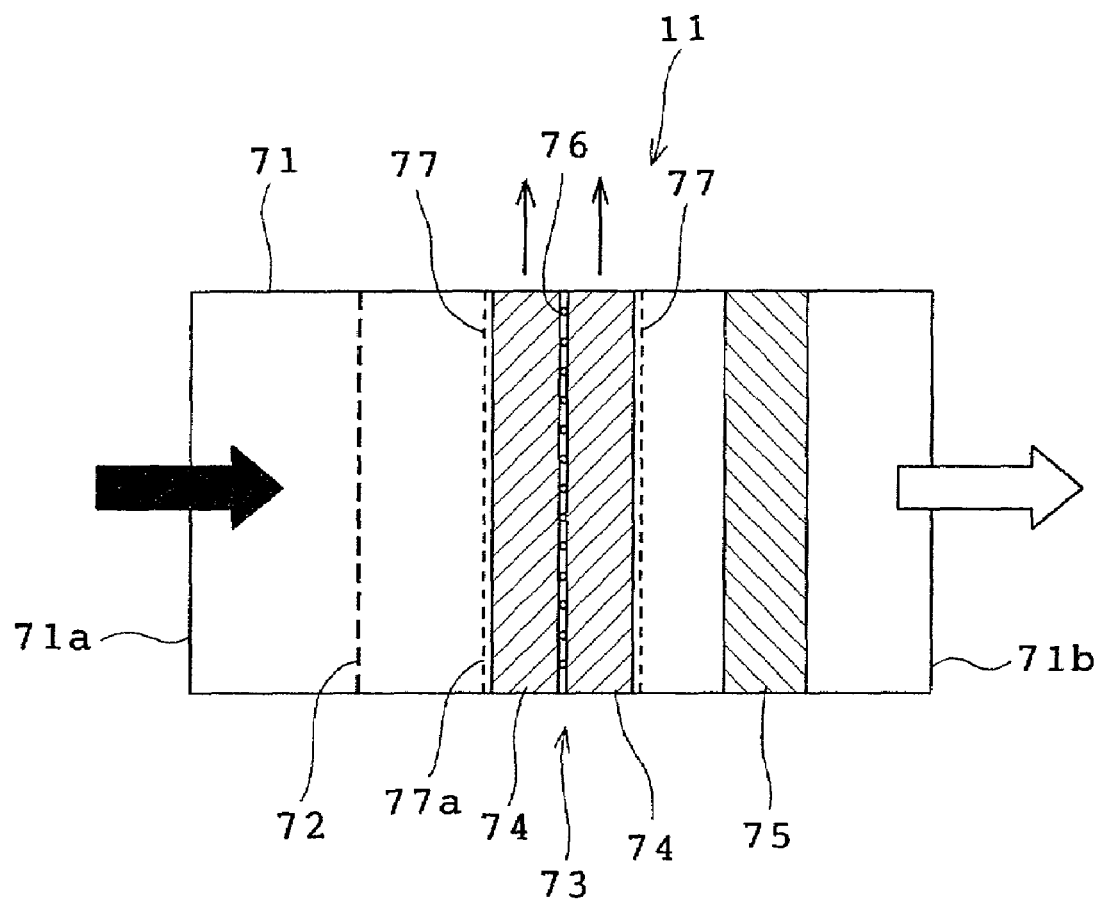
FIG. 1 is a longitudinally sectional side view of a deodorizer provided in a refrigerator of a first embodiment in accordance with the present invention.

A first embodiment of the present invention will be described with reference to FIGS. 1 to 6. Referring first to FIG. 2, a refrigerator of the first embodiment in accordance with the invention is schematically shown. The refrigerator comprises a body 1 formed into the shape of a generally rectangular box having a front opening. The refrigerator body 1 is formed by assembling an outer casing 2 and an inner casing 3 and filling a space between the casings with a heat-insulating foam 4. A horizontal partition plate 5 made of a synthetic resin is fixed to an inner face of the inner casing 3. The partition plate 5 defines a cold storage compartment 6 in an upper interior of the refrigerator body 1. A first door 7 is hingedly mounted on a front end of the cold storage compartment 6. The partition plate 5 has on an upper face thereof a plurality of protrusions (not shown) on which a chilling case 8 is placed. The chilling case 8 is formed into the shape of a container having upper and front openings. A cold air path 9 is defined between the underside of the chilling case 8 and the upper face of the partition plate 5. A lid 10 is provided for opening and closing a front opening of the chilling case 8.

Figure 3:
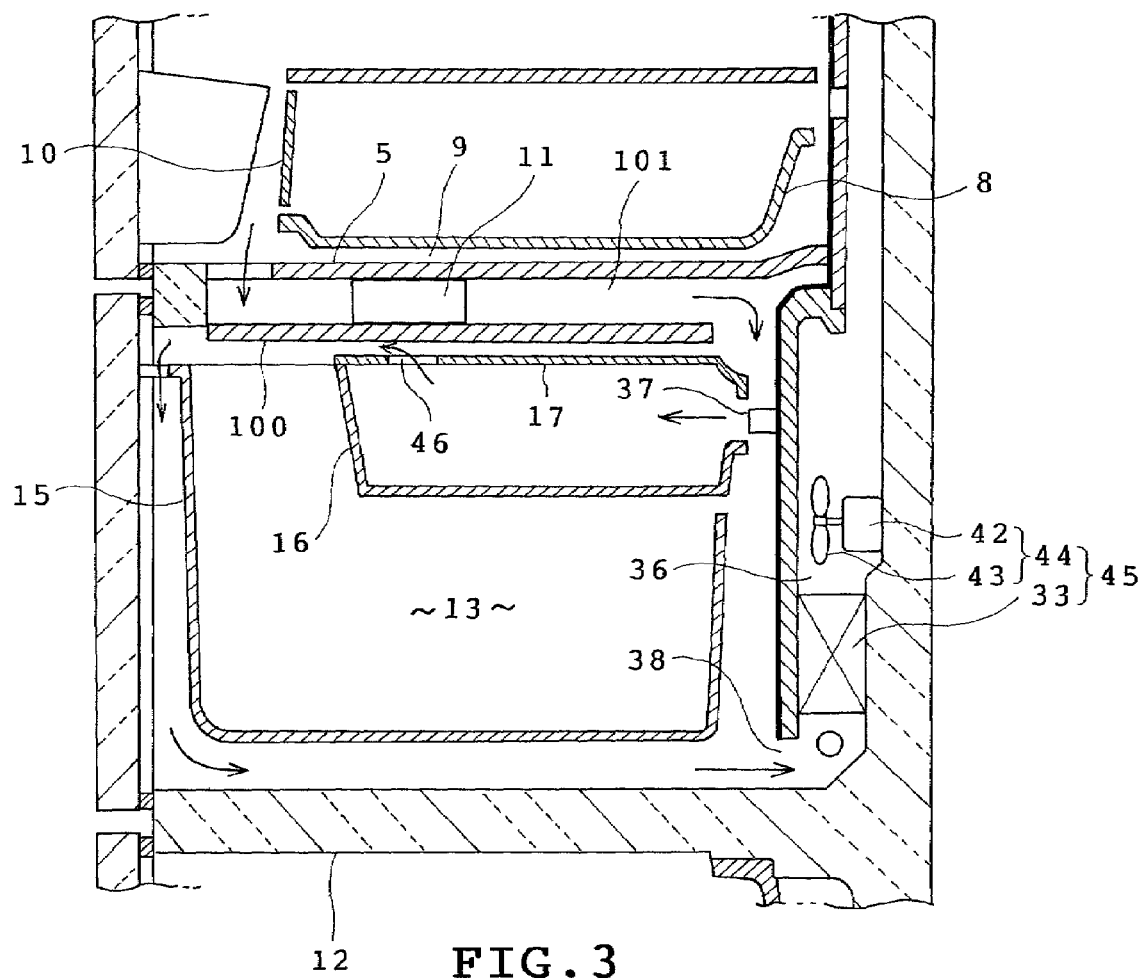
FIG. 3 is an enlarged view of a cold air path shown in FIG. 2.

A support plate 100 is fixed to the inner face of the inner casing 3 so as to be spaced from the partition plate 5 under the latter. The partition plate 5 has an open front end through which cold air is caused to flow from the cold storage compartment 6 side into a cold air path 101 (a circulation path) defined between the partition plate 5 and the support plate 100. A deodorizer 11 is provided in the cold air path 101 as shown in FIG. 3. The construction of the deodorizer 11 will be described in detail later. The support plate 100 has a rear end open to a vegetable compartment 13 (storage compartment). Cold air is caused to flow from the cold storage compartment 6 side through the cold air path 101 and the deodorizer 11 into the vegetable compartment 13.

A heat-insulating partition plate 12 is fixed to the inner face of the inner casing 3 so as to be spaced from the partition plate 5 below the latter. The heat-insulating partition plate 12 is formed by enclosing styrene foam in a casing made of a synthetic resin. The vegetable compartment 13 is thus defined between the heat-insulating partition plate 12 and the partition plate 5. The vegetable compartment 13 communicates with the cold storage compartment 6 via the deodorizer 11 located in the cold air path 101. Thus the vegetable compartment 13 serves as a part of the cold storage compartment 6. A second door 14 is mounted on a front end of the vegetable compartment 13 so as to be slidable forward and rearward. A lower case 15 accommodated in the vegetable compartment 13 is formed into the shape of a container having an upper opening. An upper case 16 is mounted on the lower case 15 so as to close an upper face of the lower case except a front end. The upper case 16 is formed into the shape of a container having an upper opening. A lid 17 is mounted on the upper case 16 so as to close and open the upper opening of the upper case.

Figure 4:
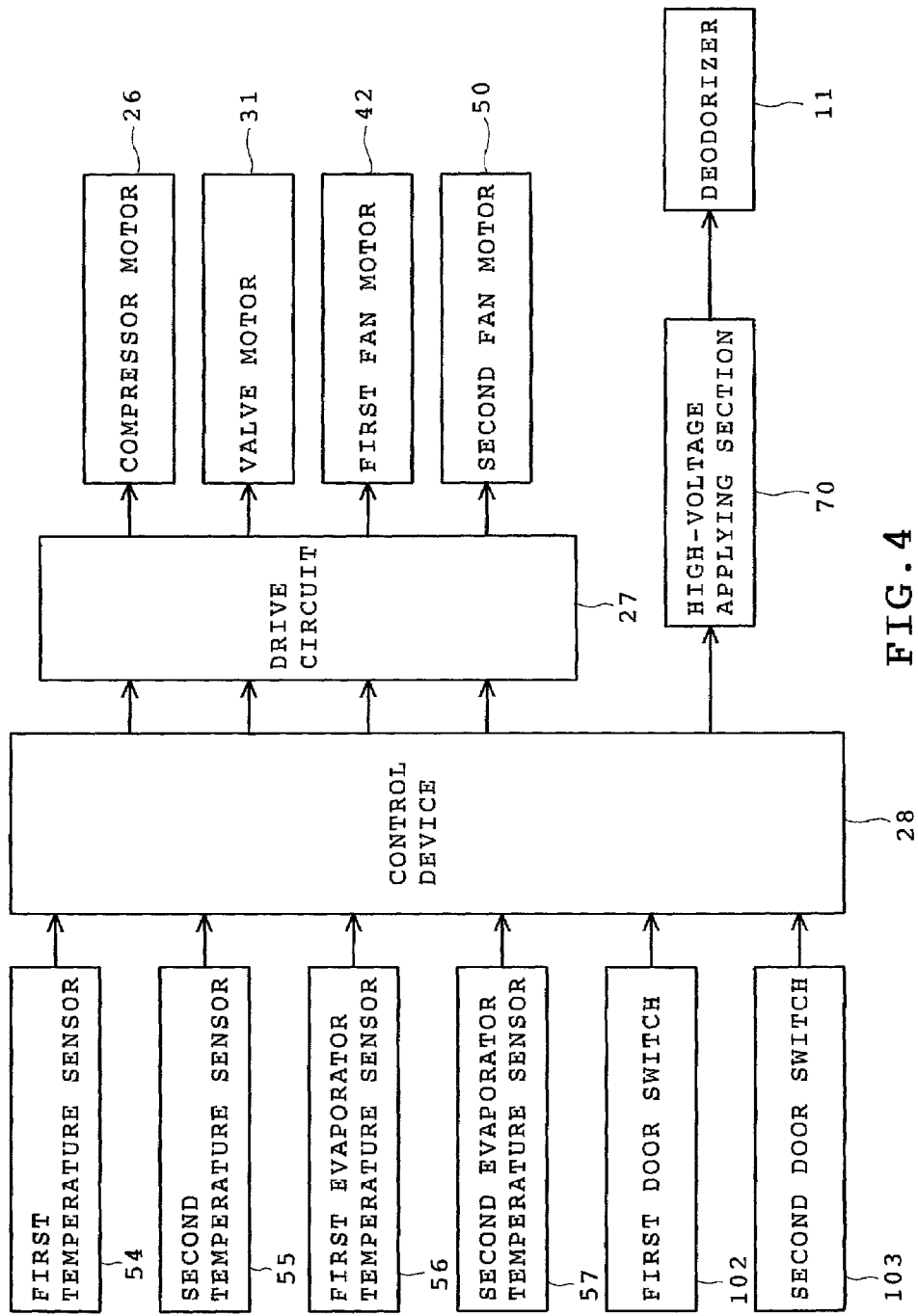
FIG. 4 is a block diagram showing an electrical arrangement of the refrigerator.

Referring to FIG. 2 again, a freezing compartment 19 is defined in the inner casing 3 so as to be located below the heat-insulating partition plate 12. Thus the freezing compartment 19 is thermally isolated from the upper cold storage compartment 6 and vegetable compartment 13. Upper and lower doors 20 and 21 are mounted on a front end of the freezing compartment 19 so as to be slidable forward and rearward. Upper and lower freezing cases 22 and 23 are disposed in the freezing compartment 19. A machine compartment 24 is defined in a lower part of the refrigerator body 1. A reciprocating compressor 25 constituting a refrigerating cycle is provided in the machine compartment 24. The compressor 25 includes a compressor motor 26 as a drive source. The compressor motor 26 is electrically connected through a drive circuit 27 to a control device 28 serving as control means and voltage changing means as shown in FIG. 4. The control device 28 comprises a microcomputer (not shown) as a main component and is provided in the refrigerator body 1.

Figure 5:
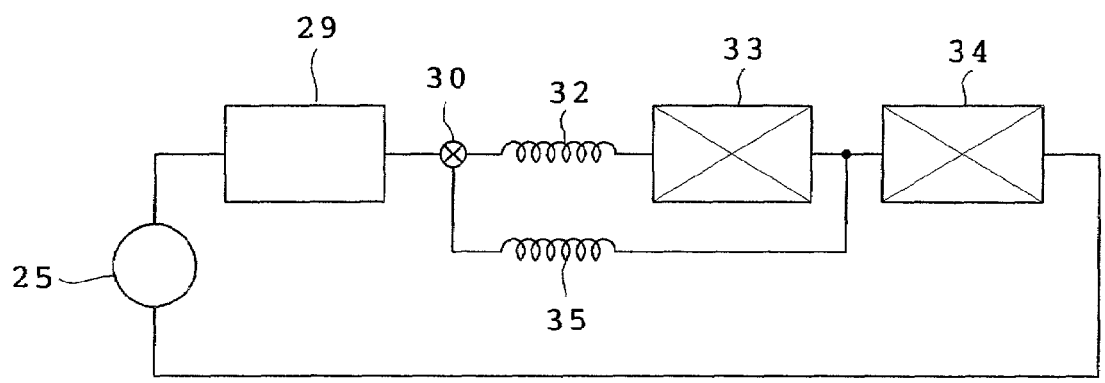
FIG. 5 illustrates a refrigerating cycle employed in the refrigerator.

The compressor 25 has a discharge opening connected via a condenser 29 constituting the refrigerating cycle to an input port of a path valve 30 as shown in FIG. 5. The path valve 30 selectively opens a first output port or a second output port on the basis of the normal or reverse rotation of a valve motor 31 (see FIG. 4). The valve motor 31 is connected via the drive circuit 27 to the control device 28. The first output port of the path valve 30 is connected via a first capillary tube 32 to an entrance of a first evaporator 33 as shown in FIG. 5. The first evaporator 33 has an exit connected to an entrance of a second evaporator 34. The second evaporator 34 has an exit connected to a suction opening of the compressor 25. When the first output port of the path valve 30 is open, refrigerant discharged from the compressor 25 is supplied into both of the first and second evaporators 33 and 34. The path valve 30 further has a second output port connected to an entrance of a second capillary tube 35. The second capillary tube 35 has an exit connected between the exit of the first evaporator 33 and the entrance of the second evaporator 34. When the second output port of the path valve 30 is open, the refrigerant discharged from the compressor 25 is supplied only to the second evaporator 34.

Returning to FIG. 2 again, a first cold air producing chamber 36 is defined in the rear of the vegetable compartment 13. The first evaporator 33 is accommodated in the first cold air producing chamber 36. The first cold air producing chamber 36 has a cylindrical cold air discharge opening 37 and a cold air suction opening 38. The cold air discharge opening 37 is inserted into the upper case 16.

A generally L-shaped duct cover 39 is fixed in the cold storage compartment 6. The duct cover 39 is made of a synthetic resin and has a plurality of cold air discharge holes 40 open to the cold storage compartment 6. The duct cover 39 constitutes a generally L-shaped cold air duct 41 in association with a rear wall of the inner casing 3. The duct 41 has an upper end open to the interior of the cold storage compartment 6 and a lower end communicating with the first cold air producing chamber 36. A first fan motor 42 is provided in the first cold air producing chamber 36 and connected via the drive circuit 27 to the control device 28. A first fan 43 (blower) is coupled with a rotational shaft of the first fan motor 42 so that cold air is circulated through the following route upon rotation of the first fan 43. A first fan unit 44 comprises the first fan motor 42 and the first fan 43. The first fan unit 44 and the first evaporator 33 constitute a first cooling unit 45. Cold air circulation path for the cold storage compartment 6 and vegetable compartment 13:

Part of air in the refrigerator is discharged from the first cold air producing chamber 36 through the cold air discharge opening 37 into the upper case 16 to be discharged in front of the upper case 16 through cold air flow holes 46 formed in the front end of the lid 17. The cold air further flows downward along the front of the lower case 15 and then rearward along the underside of the lower case, returned through the cold air suction opening 38 into the cold air producing chamber 36. In this case, the interior air is cooled by the first evaporator into cold air, which cools an atmosphere in the vegetable compartment 13. The remaining air in the first cold air producing chamber 36 is discharged through the cold air discharge holes 40 of the cold air duct 41 and the open upper end of the duct 41, then flowing into the cold air path 9 below the chilling case 8. The air further flows through the deodorizer 11 and the cold air path 101 into the vegetable compartment 13, further flowing through the holes 46 in front of the upper case 16. Thereafter, the interior air flows downward along the front of the lower case 16 and then rearward along the underside of the lower case 15 to be returned through the suction opening 38 into the first cold air producing chamber 36. In this case, the interior air is cooled by the first evaporator into cold air, which cools an atmosphere in the cold storage compartment 6 and the atmosphere in the vegetable compartment 13. More specifically, the deodorizer 52 is disposed at a return path side of the circulated cold air.

A second cold air producing chamber 47 is provided in the rear of the freezing compartment 19. A cold air discharge opening 48 and a cold air suction opening 49 are provided in upper and lower ends of the second cold air producing chamber 47 respectively. The second evaporator 34 and a second fan motor 50 are accommodated in the second cold air producing chamber 47. The second fan motor 50 is connected through the drive circuit 27 to the control device 28. The second fan 51 is coupled with a rotational shaft of the fan motor 50 so that the cold air is circulated through the following route upon rotation of the second fan 51. A second fan unit 52 comprises the second fan motor 50 and the second fan 51. The second fan unit 52 and the second evaporator 34 constitute a second cooling unit 53. Cold air circulation path for the freezing compartment 6:

Interior air in the second cold air producing chamber 47 is discharged through the cold air discharge opening 48 into the freezing compartment 19 and returned through the cold air suction opening 49 into the second cold air producing chamber 47. In this case, the interior air is cooled by the second evaporator 34 into cold air, which cools an atmosphere in the freezing compartment 19.

Referring now to FIG. 4, first and second temperature sensors 54 and 55 are provided in the cold storage and freezing compartments 6 and 19 respectively. The temperature sensors 54 and 55 comprise thermistors delivering temperature signals Vr and Vf with voltage levels according to temperatures in the cold storage and freezing compartments 6 and 19, respectively. The temperature sensors 54 and 55 are connected to the control device 28. A first evaporator temperature sensor 56 and a second evaporator temperature sensor 57 are connected to the control device 28. The first and second evaporator temperature sensors 56 and 57 comprise thermistors mounted on the first and second evaporators 33 and 34 using fixtures (not shown), respectively. The first and second evaporator temperature sensors 56 and 57 deliver temperature signals Vre and Vfe having voltage levels according to surface temperatures of the first and second evaporators 33 and 34, respectively. First and second door switches 102 and 103 are provided for detecting an open or closed state of the first and second doors 7 and 14 respectively. The signals indicative of the open or closed states of the doors are supplied to the control device 28.

The control device 28 includes an internal ROM on which an operation control program is recorded. The control device 28 controls the compressor motor 26, the valve motor 31, and the first and second fan motors 42 and 50 based on the temperature signals Vr, Vf, Vre and Vfe form the first and second temperature sensors 54 and 55 and the first and second evaporator temperature sensors 56 and 57, whereby a cooling operation is carried out. Further, the control device 28 controls the high-voltage applying section (voltage changing means) 70 so that a pulsed high voltage at minus several kilovolts is applied to the electrodes of the deodorizer 11.

Figure 2:
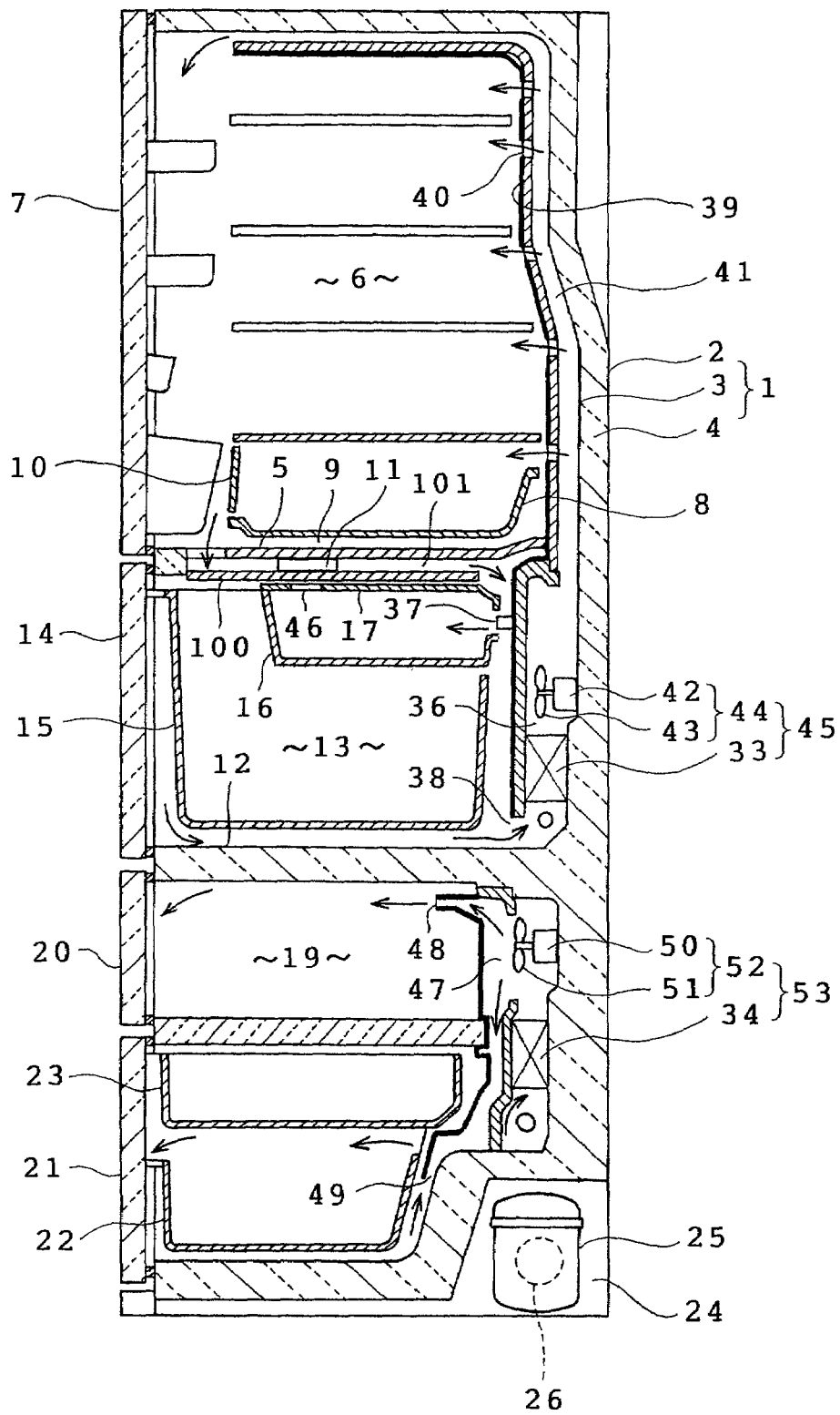
FIG. 2 is a longitudinally sectional side view of the refrigerator.

Referring to FIG. 1, a major part of the deodorizer 11 is shown. In a rectangular cylindrical blowing path 71 are disposed a prefilter 72, an electrical discharge mechanism (discharging means) 73, two photocatalyst modules 74 and an ozone decomposing catalyzer (ozone decomposing means) 75. Cold air in the refrigerator is caused to flow through a left-hand inlet 71a into the blowing path 71 upon rotation of the first fan 43 disposed in the first cold air producing chamber 36, as viewed in FIG. 1. The cold air then passes through the aforesaid elements so as to be deodorized. The deodorized cold air flows through a right-hand outlet 71b into the cold air path 101 as viewed in FIG. 1. The prefilter 72 is disposed at the uppermost stream of the blowing path 71 to remove dust from the cold air. The discharge mechanism 73 is disposed next the prefilter 72 and comprises a plurality of generally wire-shaped discharge electrodes 76 made from tungsten and two flat counter electrodes 77. The discharge electrodes 76 are disposed in one row so as to extend horizontally across the flowing cold air. The two counter electrodes 77 are disposed before and behind the discharge electrodes 76 with respect to the direction in which the cold air flows, so as to sandwich the discharge electrodes. Each counter electrode 77 has a number of slits 77a through which the cold air is caused to flow. A high voltage of the negative polarity is applied across the discharge electrodes 76 and the counter electrodes 77 so that ultraviolet rays each having a wavelength not exceeding 380 nm and ozone are produced.

Each photocatalyst module 74 is provided between the discharge electrodes 76 and the counter electrodes 77. Each photocatalyst module 74 comprises a base made from a porous ceramic such as alumina or silica. A photocatalytic material such as titanium oxide is applied to a surface of the base and then dried or fired so as to be fixed to the surface of the base. The discharge mechanism 73 is detachably attached to the blowing path 71 in the direction of arrow in FIG. 1 together with the photocatalyst modules 74. More specifically, an openable door (not shown) is mounted on a pipe wall of the blowing path 71 so as to correspond to a location of the discharge mechanism 73. When the door is opened, the discharge mechanism 73 and the photocatalyst modules 74 both disposed in the blowing path 71 are taken out in the direction of arrow in FIG. 1.

The operation of the refrigerator will now be described. A case will first be described where the cooling operation is carried out on the basis of information about a set temperature for the cold storage compartment 6 and temperature information obtained by the first temperature sensor. In this case, the control device 28 opens the second output port of the flow valve 30 so that the refrigerant discharged from the compressor 25 is supplied into the first evaporator 33. The control device 28 further drives the first fan unit 45 so that the cold air is circulated through the cold storage and vegetable compartments 6 and 13. When the operation of the deodorizer 11 is then initiated, the high-voltage discharge is performed between the discharge electrodes 76 and the counter electrodes 77 such that the ultraviolet rays and ozone are produced.

The cold air containing odor component in the refrigerator flows through the inlet 71a into the deodorizer 11 as the result of rotation of the first fan 43. The cold air is then filtrated by the prefilter 72, thereafter reaching the discharge mechanism 73 through the slits 77a of the counter electrodes 77. In the discharge mechanism 73, the ultraviolet rays produced by the high-voltage discharge are irradiated onto the photocatalyst modules 74. When subjected to light energy, the titanium oxide is activated to perform the photocatalytic action. Consequently, the odor component contained in the circulated cold air, such as ammonia, is decomposed by oxidation. Furthermore, when passing through the discharge mechanism 73, the circulated cold air is mixed with the ozone produced by the high-voltage discharge, reaching the ozone decomposing catalyzer 75 disposed down the discharge mechanism 73 with respect to the direction in which the circulated cold air flows. The ozone mixed with the odor component etc. in the circulated cold air is decomposed by the catalyzer 75 to thereby produce active oxygen. The odor component etc. is decomposed by the active oxygen. The cold air thus deodorized in the aforesaid manner is recirculated through the outlet 71b into the compartments of the refrigerator.

Figure 6:
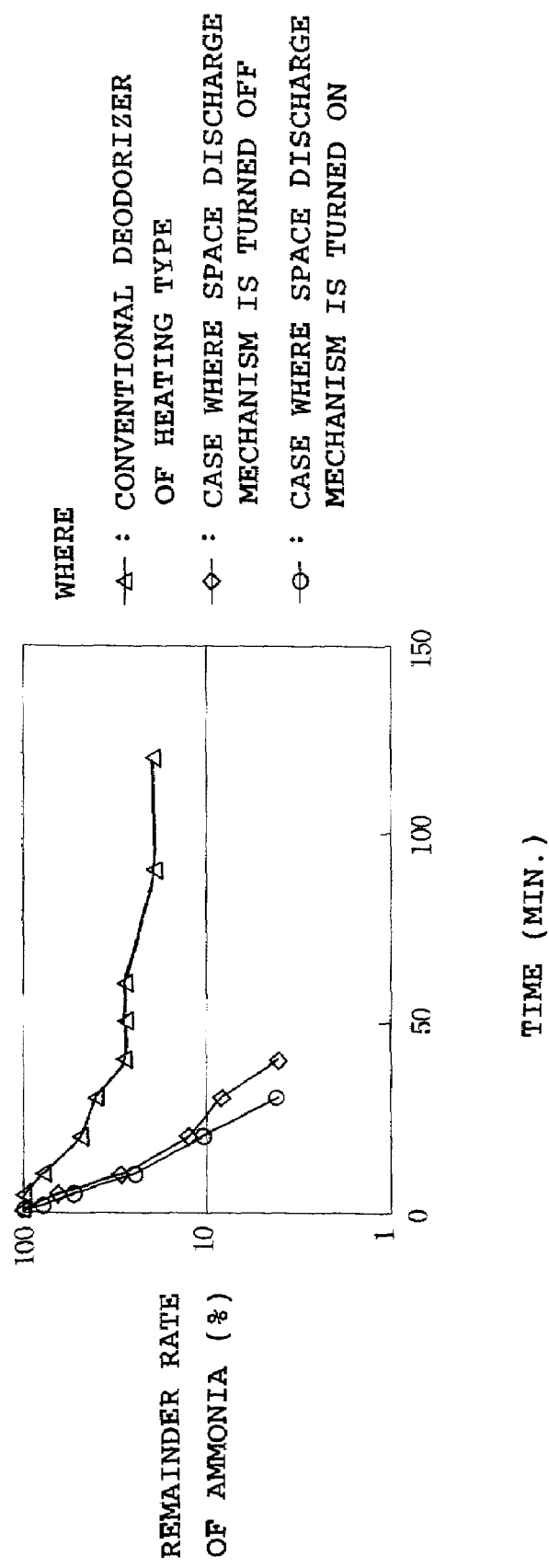
FIG. 6 is a graph showing the results of an experiment conducted by the inventors.

FIG. 6 shows the results of an experiment conducted by the inventors. A remainder rate (%) of ammonia in the refrigerator with lapse of time was measured in the case where the ammonia in the refrigerator was decomposed by several types of deodorizers. Symbol "Δ" denotes the case of a conventional deodorizer of the heating type. Symbol "◇" denotes the case of the deodorizer of the embodiment when the electric discharge was carried out by the discharge mechanism 73 (ON). Symbol "○" denotes the case of the deodorizer of the embodiment when the electric discharge was not carried out by the discharge mechanism 73 (OFF).

As obvious from FIG. 6, even when the discharge mechanism was turned off, the remainder rate of ammonia was reduced to a larger extent as compared with the case of the conventional deodorizer. A still more desirable characteristic was obtained from the case of the deodorizer of the embodiment when the discharge mechanism was turned off.

According to the above-described embodiment, the deodorizer 11 is disposed in the cold air path 101 of the refrigerator. The discharge mechanism 73, the photocatalyst modules 74 and the ozone decomposing catalyzer 75 are disposed in the blowing path 71 of the deodorizer 11. The ultraviolet rays are produced by the high-voltage discharge of the discharge mechanism 73. The ultraviolet rays cause the photocatalyst modules 74 to perform the photocatalytic action. Further, the ozone resulting from the high-voltage discharge is decomposed by the ozone decomposing catalyzer 75. Consequently, the odor component and injurious component are decomposed by oxidation. Thus, decomposition and elimination of the odor component etc. present in the refrigerator are carried out using the ozone and ultraviolet rays both produced by the high-voltage discharge. Consequently, an adsorbent for deodorization need not be replaced by a new one, and drug need not be supplemented. Further, since the photocatalytic action and the ozone decomposing action are combined together, a wider range of odor component can be decomposed. Additionally, since the deodorizer 11 can produce the ultraviolet rays without using a fluorescent lamp, no special handling is required in the case of disposition of the refrigerator or the deodorizer 11.

Further, since the deodorizer 11 decomposes the ozone by means of the ozone decomposing catalyzer 75, the ozonic concentration in the atmosphere in the cold storage or vegetable compartment 6 or 13 can be prevented from an excessive increase and accordingly, the user can be prevented from having a smell of ozone (in the concentration ranging between 0.02 and 0.03 ppm, for example) when opening the door 7 or 14 of the refrigerator or components in the interior of the refrigerator can be prevented from corrosion.

Further, the discharge mechanism 73 is detachably attached to the blowing path 71. Accordingly, when contaminant is adherent to the discharge electrodes 76, the counter electrodes 77 or the photocatalyst modules 74, the discharge mechanism 73 is detached from the deodorizer body so that the contaminant is eliminated by water washing, for example. Additionally, the discharge mechanism 73 comprises a plurality of generally wire-shaped discharge electrodes 76 and two flat counter electrodes 77. Accordingly, a larger space for deodorization can be obtained as compared with a surface discharge system in which electric discharge is performed via an insulator. Further, since the high voltage of the negative polarity is applied across the discharge electrodes 76 and the counter electrodes 77, a larger amount of ozone can be produced and accordingly, the deodorizing efficiency can be improved.

The voltage application to the discharge mechanism 73 is synchronized with the operation of the first fan 43. Further, the voltage applied to the discharge mechanism 73 is changed according to a volume of air supplied by the first fan 43. Accordingly, deodorization can efficiently be performed in the case where the deodorizer 11 is operated when the circulated cold air flows into the blowing path 71. The applied voltage is increased as the rotational speed of the first fan 43 is decreased such that a flow rate of cold air is reduced. Consequently, a reduction in the deodorizing efficiency with the reduction in the flow rate of cold air can be compensated.

Since each photocatalyst module 74 is disposed between the electrodes 76 and 77 of the discharge mechanism 73, non-directional ultraviolet rays produced by the discharge mechanism 73 can efficiently be irradiated onto each photocatalyst module 74 and accordingly, the efficiency in the photocatalytic reaction can be improved. Furthermore, the photocatalyst modules 74 are disposed at the upstream and downstream sides of the discharge mechanism 73. Consequently, the ultraviolet rays produced in the discharge mechanism 73 can be used further efficiently. Additionally, each photocatalyst module 74 is formed by fixing titanium oxide to the surface of the base made from the porous ceramic. Consequently, the flow of cold air can be prevented from being blocked by each photocatalyst module 74 even when each module is disposed in the blowing path 71. Further, since an area of the base surface to which titanium oxide is fixed is rendered larger, the photocatalytic reaction can be performed with high efficiency even when an amount of titanium oxide which is an expensive material is reduced as much as possible, whereupon the injurious matter can efficiently be eliminated.

Figure 7:
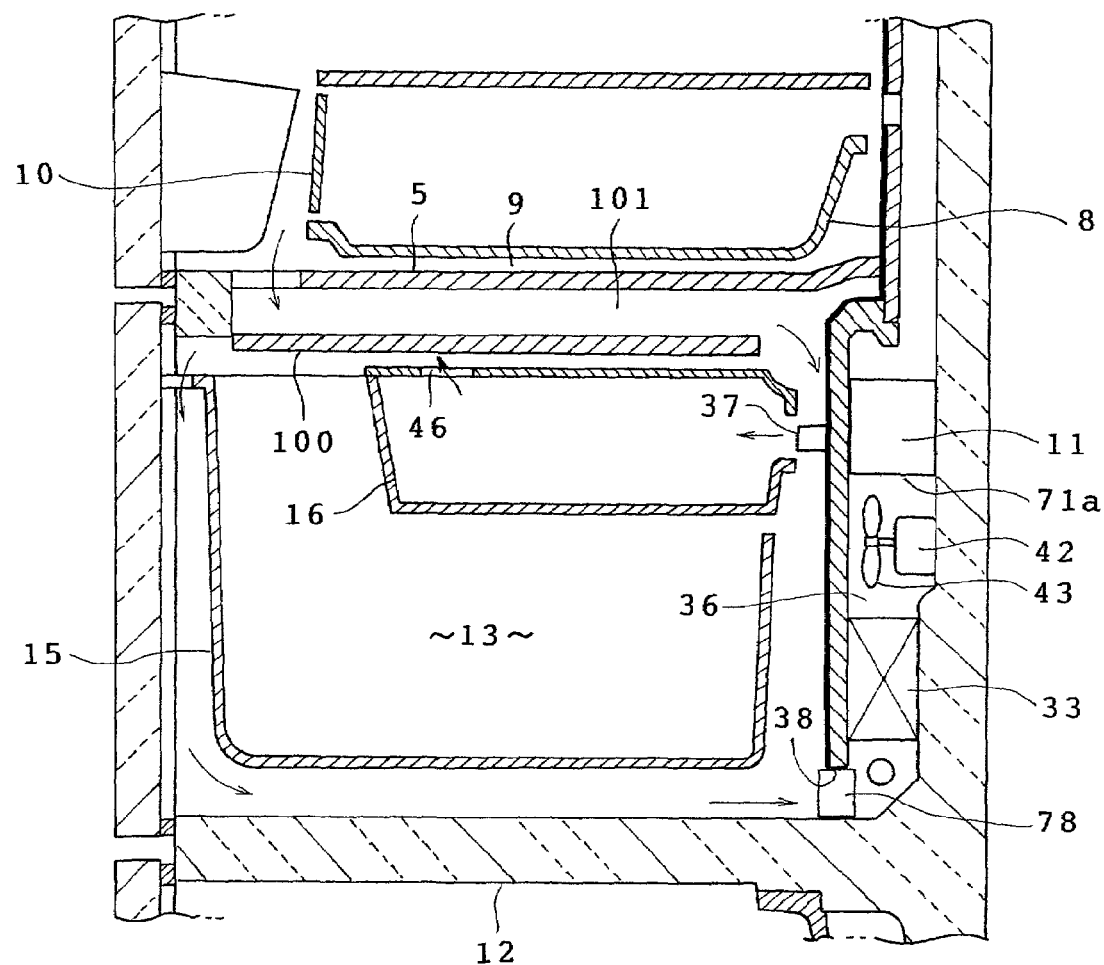
FIG. 7 is an enlarged longitudinally sectional side view of a first cold air producing chamber of the refrigerator of a second embodiment in accordance with the invention.

FIG. 7 illustrates a second embodiment of the invention. Only the differences between the first and second embodiments will be described, and identical or similar parts in the second embodiment are labeled by the same reference symbols as in the first embodiment. In the second embodiment, the deodorizer 11 is disposed above the first fan 43 in the first cold air producing chamber 36 with the inlet 71a being located at the first fan 43 side. The ozone decomposing catalyzer 78 is disposed in the cold air suction opening 38 of the first cold air producing chamber 36. The other construction of the refrigerator is the same as that in the first embodiment.

According to the second embodiment, ozone can be decomposed also at the cold air inlet 38 by the ozone decomposing catalyzer 78. Consequently, the first evaporator 33 and the other piping disposed in the first cold air producing chamber 36 can reliably be prevented from being corroded by the ozone. In the construction of the second embodiment, the ozone concentration is at or below 0.05 ppm in order that the corrosion may be prevented.

Figure 8:
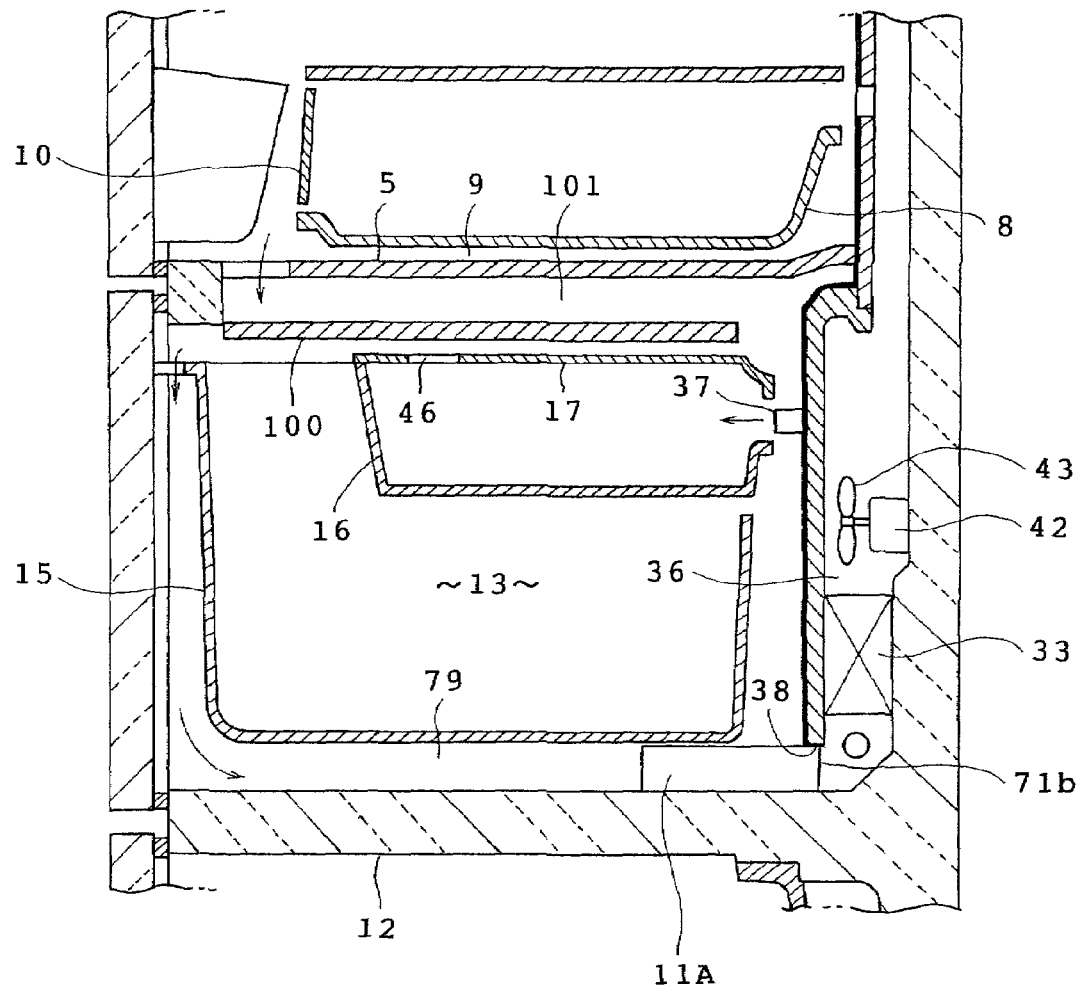
FIG. 8 is an enlarged longitudinally sectional side view of a vegetable compartment of the refrigerator of a third embodiment in accordance with the invention.
Figure 9A:
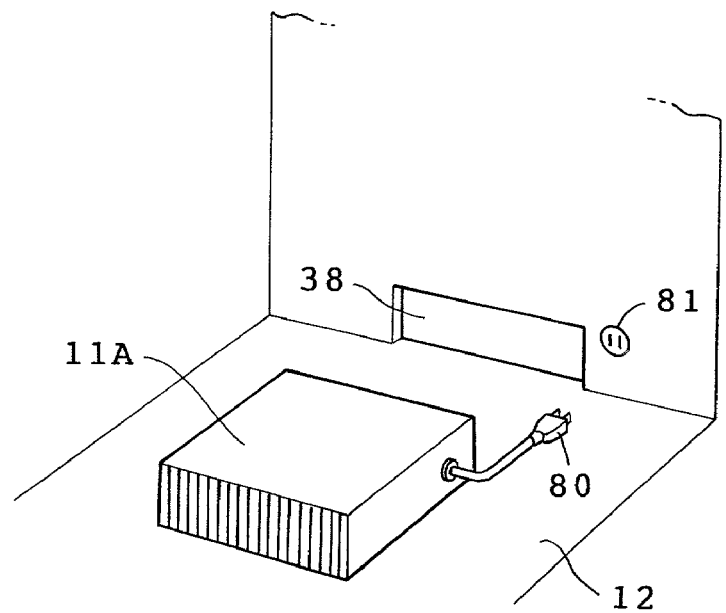
FIGS. 9A and 9B are perspective views of the vegetable compartment with a lower case being eliminated, showing the states before and after attachment of the deodorizer respectively.
Figure 9B:
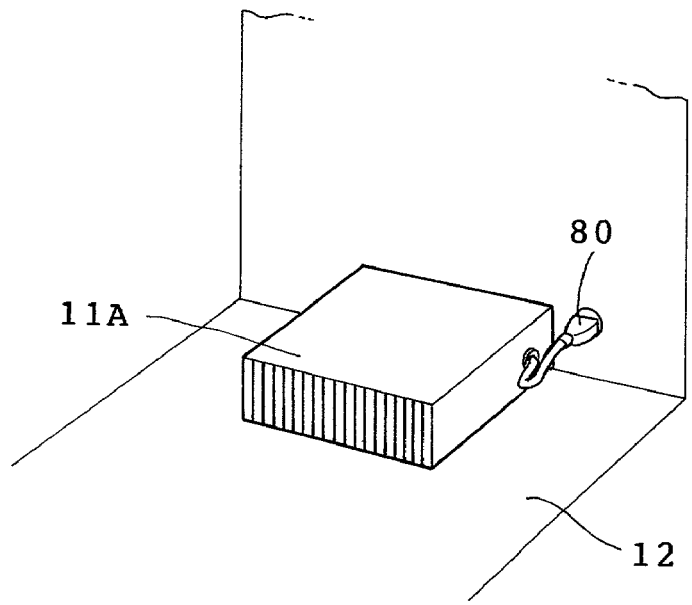

FIGS. 8, 9A and 9B illustrate a third embodiment. In the third embodiment, the deodorizer 11A is discrete from the refrigerator body 1. The deodorizer 11A is detachably attached to the refrigerator body 1. The deodorizer 11A is disposed in the cold air path 79 defined between the lower case 15 and the heat-insulating partition plate 12 in the vegetable compartment 13 as shown in FIG. 8. The outlet 71b of the deodorizer 11A communicates with the cold air suction opening 38 of the first cold air producing chamber 36.

A power-supply plug 80 for supplying AC 100 V extends from the right-hand rear end of the deodorizer 11A as shown in FIG. 9A. When the deodorizer 11A is attached to the refrigerator, the power-supply plug 80 is inserted into a socket 81 provided by the side of the cold air suction opening 38 as shown in FIG. 9B.

According to the third embodiment, the deodorizer 11A is detachably attached to the refrigerator body 1. Accordingly, when contaminant is adherent to the discharge electrodes 70, the counter electrodes 77 or the photocatalyst modules 74, the discharge mechanism 73 is taken out of the deodorizer body so that the contaminant is removed by water washing etc. as in the first embodiment. For example, refrigerators for commercial use and for insulated vans have a larger capacity and accordingly, a large amount of odor component is contained in the interior atmosphere of the refrigerators. As a result, maintenance needs to be frequently carried out. Thus, when the invention is applied to such a refrigerator having a large capacity, the maintenance can readily be performed.

Figure 10:
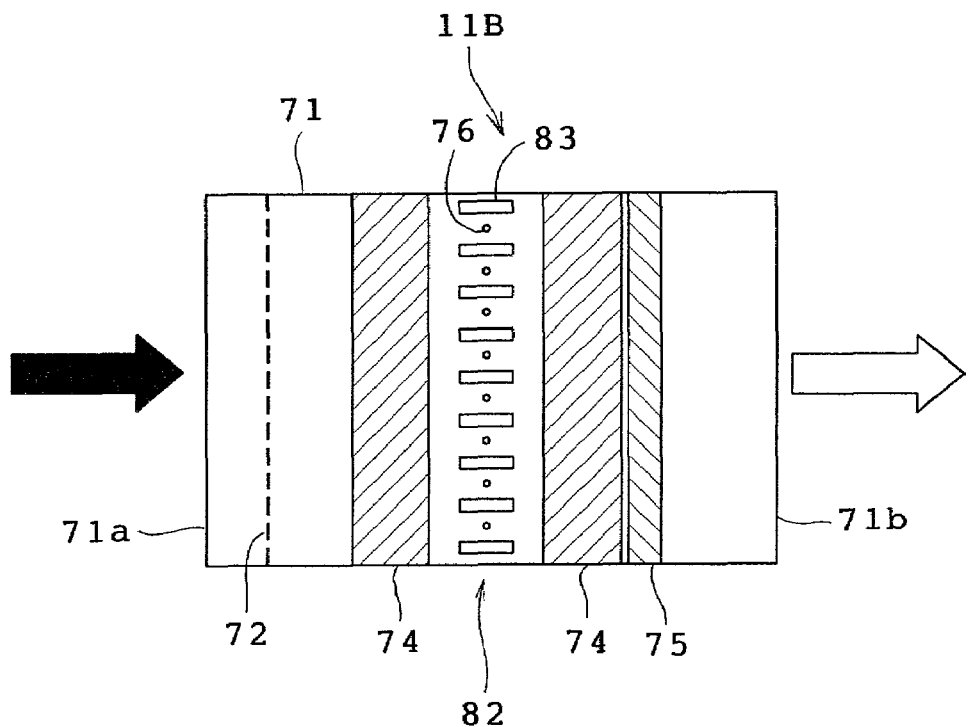
FIG. 10 is a view similar to FIG. 1, showing the refrigerator of a fourth embodiment in accordance with the invention.
Figure 11:
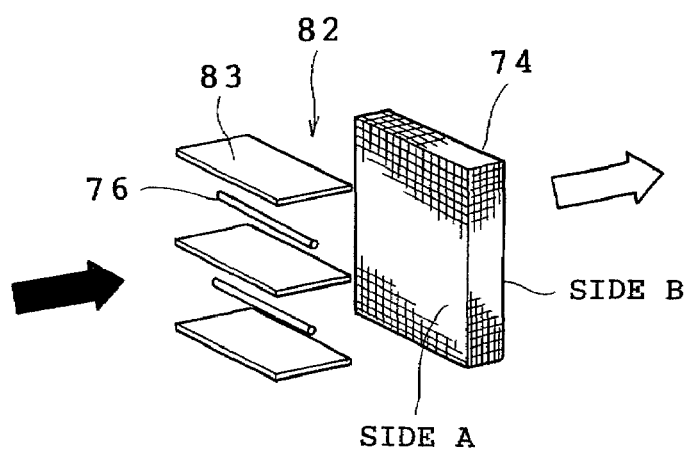
FIG. 11 is an exploded perspective view showing an electrical discharge mechanism and a photocatalyst module.

FIGS. 10 and 11 illustrate a fourth embodiment. Only the differences between the first and fourth embodiments will be described. In the fourth embodiment, the deodorizer 11B includes a discharge mechanism (discharging means) 82 comprising a plurality of counter electrode strips 83 (the number of discharge electrodes 76 plus one). The counter electrode strips 83 and the discharge electrodes 76 are alternately disposed so that flat sides of the strips are parallel to one another. Two photocatalyst modules 74 are disposed at the upstream and downstream sides of the discharge mechanism 82 respectively. The discharge mechanism 82 is detachably attached to the blowing path 71. Each photocatalyst module 74 discrete from the discharge mechanism 82 is also detachably attached to the blowing path 71.

The deodorizer 11B operates substantially in the same manner as the deodorizer 11 in the first embodiment. In the fourth embodiment, the counter electrodes 83 are disposed so that the flat sides thereof are parallel to one another. Consequently, the counter electrodes 83 do not prevent the cold air from flowing in the blowing path 71. Furthermore, when each photocatalyst module 74 having two sides A and B is attached to the blowing path 71, the side A confronting the mechanism 82 side and a side B opposed to the side A are changeable with each other. More specifically, contaminant is easy to adhere to the side A of each module 74 since the side A confronting the discharge mechanism 82 is subjected to an active photocatalytic reaction. Accordingly, when each module 74 is detached at a certain stage of adherence of contaminant and the sides A and B are changed with each other before water washing, the photocatalytic reaction can desirably be executed temporarily using the side B to which few contaminant is adherent.

According to the fourth embodiment, the side A confronting the mechanism 82 side and a side B opposed to the side A are changeable with each other when each photocatalyst module 74 is attached to the deodorizer 11B. Even when the photocatalytic reaction is reduced with a certain amount of contaminant adherent to the side A, the photocatalytic reaction can temporarily be activated as the result of change of the sides A and B with each other. Thus the photocatalyst module 74 can be used more effectively.

Figure 12:
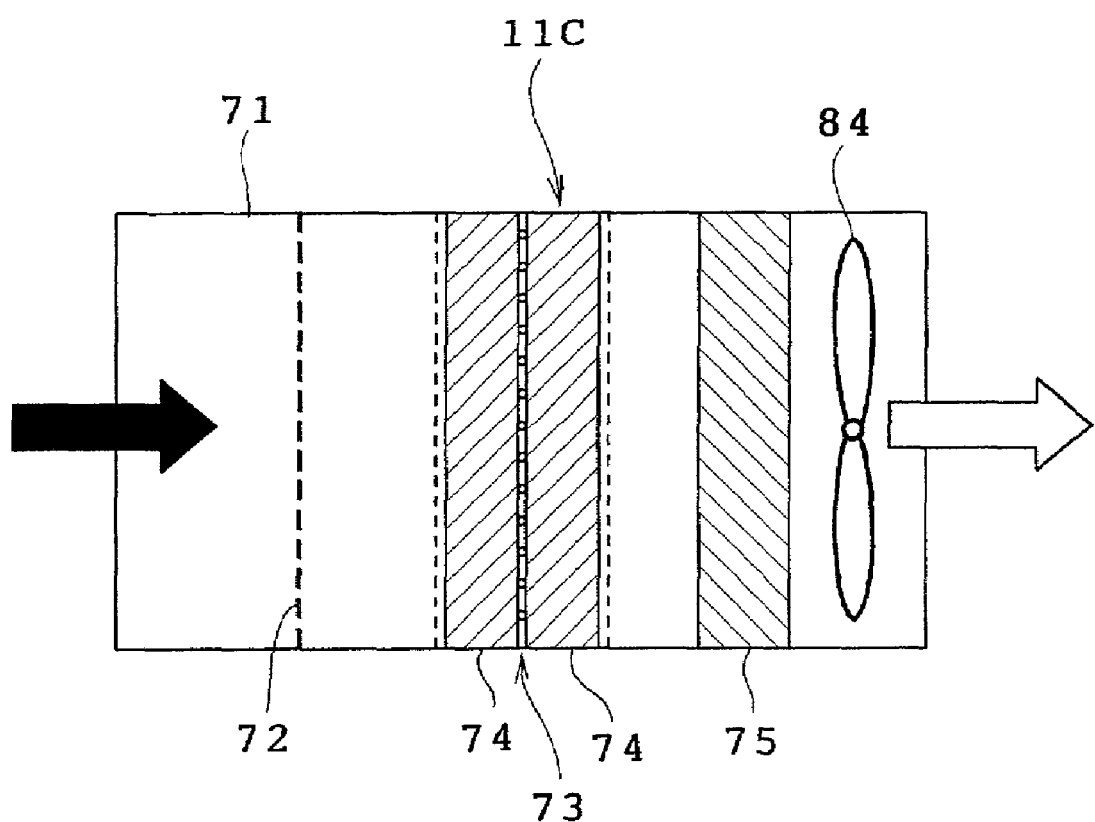
FIG. 12 is a view similar to FIG. 1, showing the refrigerator of a fifth embodiment in accordance with the invention.

FIG. 12 illustrates a fifth embodiment. Only the differences between the first and fifth embodiments will be described. In the fifth embodiment, the deodorizer 11C includes a built-in blowing fan 84 provided in the body thereof. The other construction of the deodorizer is the same as in the first embodiment. The fan 84 can be operated independently of the first fan 43. Accordingly, even when the operation of the first fan 43 is interrupted during the energy-saving operation or defrosting operation of the refrigerator, the fan 84 is operated so that the deodorizer 11C performs the deodorizing operation. Additionally, the deodorizer of the fifth embodiment can be applied to refrigerators of the direct-cooling system.

Figure 13:
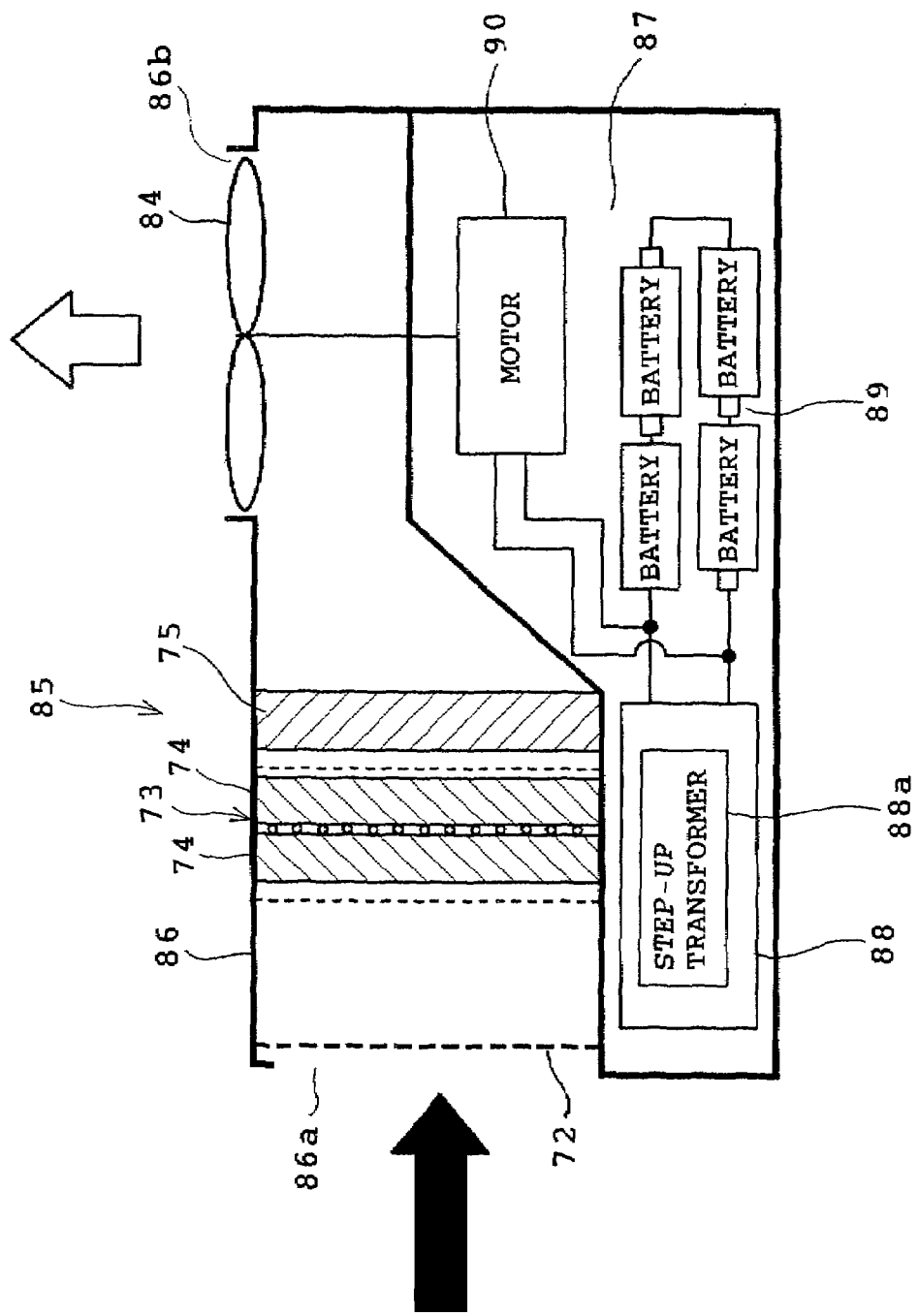
FIG. 13 is a view similar to FIG. 1, showing the refrigerator of a sixth embodiment in accordance with the invention.

FIG. 13 illustrates a sixth embodiment. In the sixth embodiment, the deodorizer 85 can be powered by a battery. Accordingly, the deodorizer 85 is operable independently of the refrigerator body 1. More specifically, the machine compartment 87 is defined below the blowing path 86 as shown in FIG. 13. In the machine compartment 87 are enclosed a high-voltage applying section 88 including a step-up transformer 88a, batteries 89, an electric motor (DC motor) 90 for driving the blowing fan 84. The blowing path 86 has an upwardly directed outlet 86b as viewed in FIG. 13. The blowing path 86 is thus formed into a generally L-shape.

The high-voltage applying section 88 includes an AC converting section (not shown) for converting a DC power supply from the batteries 89 to a corresponding AC which is stepped up by the step-up transformer 88a and then converted to a corresponding DC by a DC converting section (not shown) provided at a secondary side of the step-up transformer 88a. Finally, a pulsed high voltage of the negative polarity is applied across the discharge electrodes 76 and the counter electrodes 77 in the same manner as in the first embodiment.

According to the sixth embodiment, the deodorizer 85 is driven by the batteries 89 with the use of the step-up transformer 88a, whereupon the deodorizer 85 is discrete from the refrigerator. Consequently, the deodorizer 85 can be disposed at any location in the refrigerator, for example, near food emitting a more offensive smell, such that deodorization can efficiently be performed. Further, when the deodorizer 85 is disposed in a refrigerator without a deodorizing function, deodorization can be performed.

Figure 14:
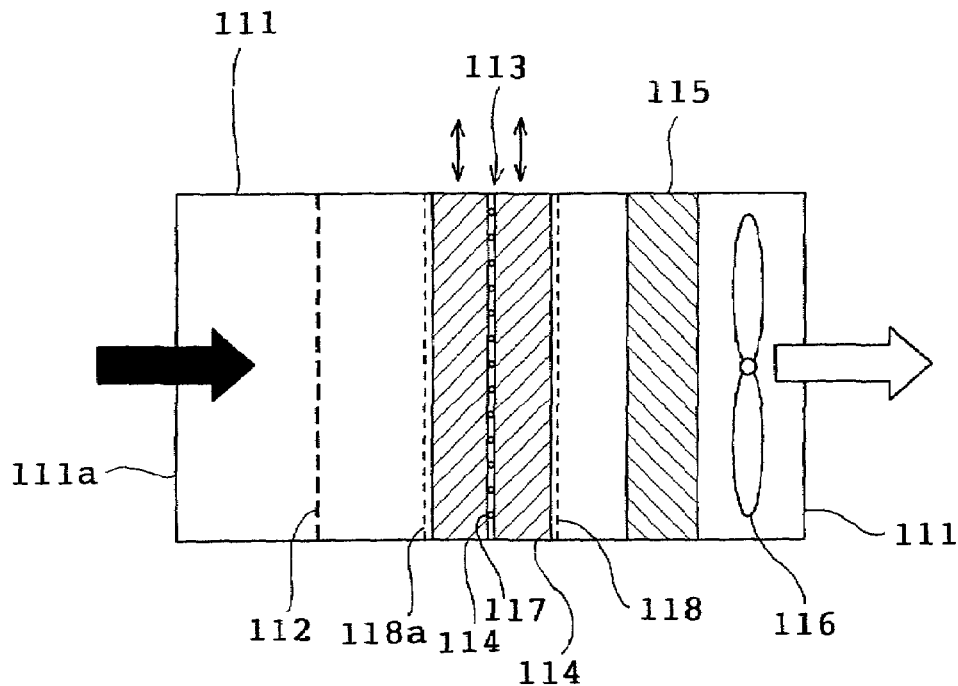
FIG. 14 is a longitudinally sectional side view of the deodorizer of a seventh embodiment in accordance with the invention.
Figure 15:
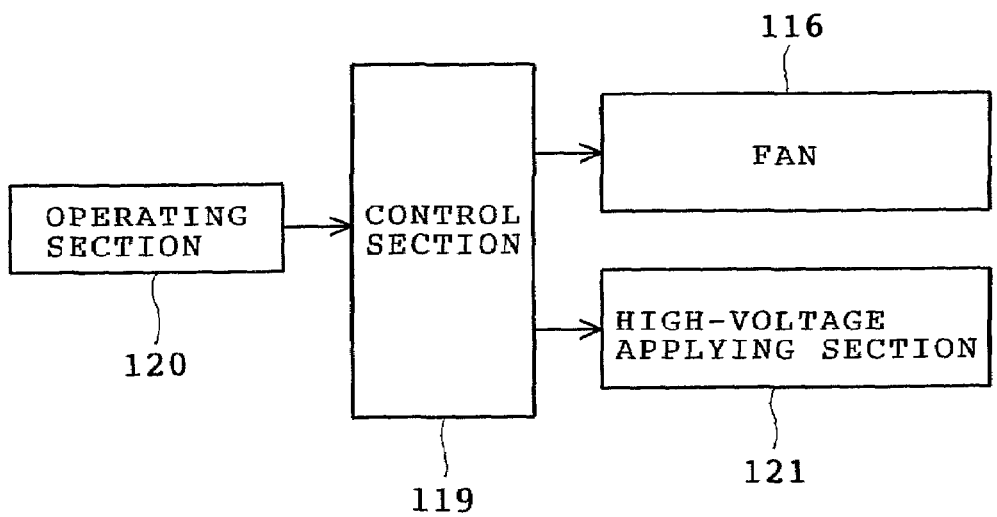
FIG. 15 is a schematic block diagram showing an electrical arrangement of the deodorizer.
Figure 16:
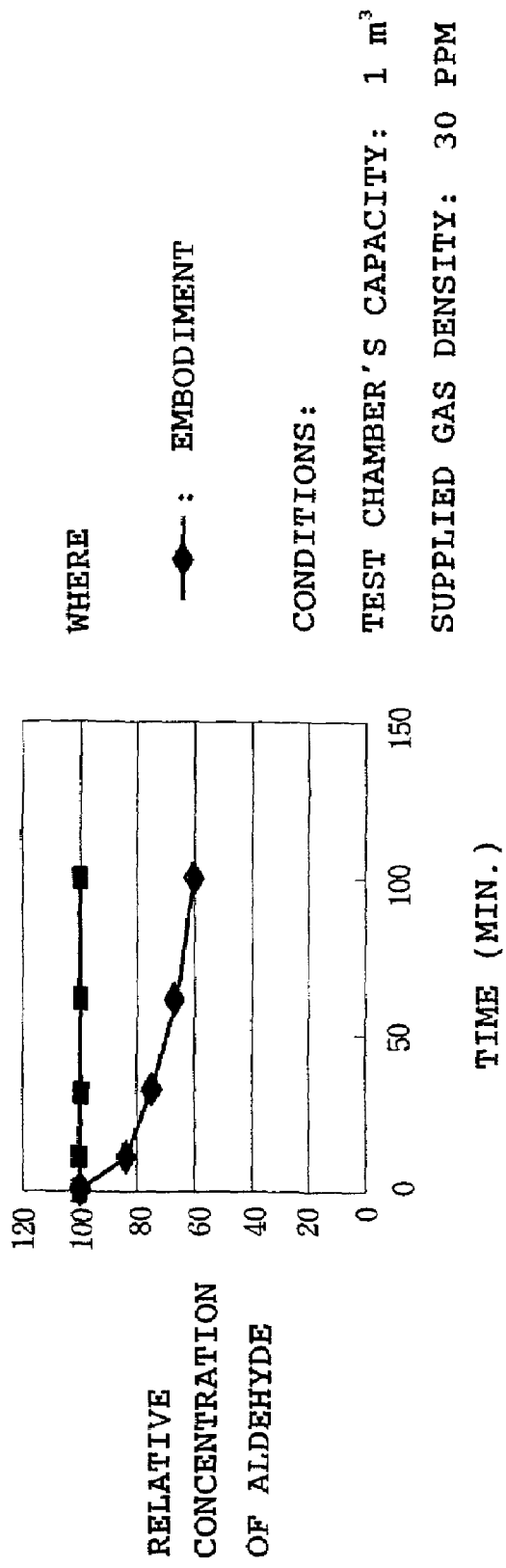
FIG. 16 is a graph showing the results of an experiment conducted with use of the deodorizer of the seventh embodiment by the inventors.

FIGS. 14 to 16 illustrate a seventh embodiment of the invention. In a duct-like blowing path 111 are disposed a prefilter 112, a discharge mechanism (discharging means) 113, two photocatalyst modules 114 and an ozone decomposing catalyzer (ozone decomposing means) 115. A fan 116 is disposed in a right-hand end of the blowing path 111 as viewed in FIG. 14. Upon rotation of the fan 116, air in a room is caused to flow through the left-hand inlet 111a into the blowing path 111 as viewed in FIG. 14. The air then passes through the aforesaid elements so as to be deodorized. The deodorized air is caused to exit through a right-hand outlet 111b.

The prefilter 112 is disposed at the uppermost stream of the blowing path 111 to remove dust from the air. The discharge mechanism 113 is disposed next the prefilter 112 and comprises a plurality of generally wire-shaped discharge electrodes 117 made from tungsten etc. and two flat counter electrodes 118. The discharge electrodes 117 are disposed in one row so as to extend horizontally across the flowing air. The two counter electrodes 118 are disposed before and behind the discharge electrodes 76 with respect to the direction in which the air flows, so as to sandwich the discharge electrodes. Each counter electrode 118 has a number of slits 118a through which the air is caused to flow.

Referring to FIG. 15, a control section 119 serving as the control means controls the deodorizer and mainly comprises a microcomputer (not shown). An operating section 120 includes a start switch, a switch for setting an operational state such as wind speed (air flow rate), etc. These switches generate respective operation signals, which are delivered to the control section 119. The control section 119 further controls the fan 116 and a high-voltage applying section 121 according to operation signals delivered thereto from the operating section 120. The high-voltage applying section 121 comprises a step-up transformer in which a step-up ratio is variable. The high-voltage applying section 121 applies a step-up pulsed DC voltage at minus several kilovolts to the discharge electrodes 117. The counter electrode 118 are grounded. Ultraviolet rays each having a wavelength not exceeding 380 nm and ozone are produced by the high-voltage discharge between the discharge electrodes 117 and the counter electrodes 118. In this case, the control section 119 controls the rotational speed of the fan 116 according the operation by the user so that a flow rate of air caused to flow through the blowing path 111 is controlled and so that the voltage applied to the discharge electrodes 117 is controlled according to a set air flow rate.

The photocatalyst modules 114 are disposed between the discharge electrodes 117 and the counter electrodes 118 respectively. Each photocatalyst module 114 comprises a base made from a porous ceramic such as alumina or silica. A photocatalytic material such as titanium oxide is applied to a surface of the base and then dried or fired so as to be fixed to the surface of the base. The discharge mechanism 113 is detachably attached to the blowing path 11 constituting the body of the deodorizer together with the photocatalyst modules 114. More specifically, an openable door (not shown) is mounted on a pipe wall of the blowing path 111 so as to correspond to a location of the discharge mechanism 113. When the door is opened, the discharge mechanism 113 and the photocatalyst modules 114 both disposed in the blowing path 111 are taken out in the direction of arrow in FIG. 14.

The ozone decomposing catalyzer 115 includes a core and a catalyzing component fixed to the core. The core comprises a manganese oxide-based ceramic honeycomb (a product) or is made by forming a metal honeycomb into the shape of a rectangular plate. The catalyzer 115 with the honeycomb structure provides a large area of contact with ozone or odor component, improving a decomposing efficiency.

The operation of the deodorizer will now be described mainly with reference to FIG. 16. When the user operates the start switch of the operating section 120, the fan 116 is rotated and the high-voltage applying section 121 is driven to apply the high voltage at minus several kilovolts to the discharge electrodes 117, under the control of the control section 119. As a result, the high-voltage discharge is performed between the discharge electrodes 117 and counter electrodes 118 so that ultraviolet rays and ozone are produced. In this case, air containing odor component in the refrigerator is caused to flow through the inlet 111a into the blowing path 111 upon rotation of the fan 116. The air then passes through the prefilter 112 to be filtered, further flowing through the slits 118a into the discharge mechanism 113. In the discharge mechanism 113, the ultraviolet rays produced by the high-voltage discharge are irradiated onto the photocatalyst modules 114 such that the titanium oxide is activated in subject to light energy of the ultraviolet rays thereby to perform the photocatalytic action. As a result, odor component contained in the air, such as ammonia, NOx, and other organic matter and injurious matter such as formaldehyde are decomposed by oxidation.

Furthermore, when passing through the discharge mechanism 113, air is mixed with ozone produced by the high-voltage discharge, further flowing into the ozone decomposing catalyzer 115. The ozone mixed with the odor component in the air is decomposed by the catalyzer 115 such that active oxygen is produced. The odor component is oxidized by the active oxygen thereby to be decomposed. The air deodorized as described above is caused to flow through the outlet 111b into the room.

The control section 119 sets the step-up voltage in the high-voltage applying section 121 at about −7 kV (peak value) when a flow rate of air flowing through the path 111 is set at about 100 m$^3$/h in the operating section 120, for example. When the flow rate of air flowing through the path 111 is set at about 50 m$^3$/h, the control section 119 sets the step-up voltage at about −10 kV. The reason for this setting is that when a flow rate of air treated by the deodorizer is reduced, the discharge voltage is increased for increase in the deodorizing performance so that the deodorizing efficiency is prevented from being reduced.

FIG. 16 shows the results of an experiment conducted by the inventors. In the experiment, a test chamber with the capacity of 1 m$^3$ was filled with 30 ppm of formaldehyde gas. The deodorizer of the seventh embodiment was placed in the test chamber to be operated. The relative concentration of the formaldehyde gas was measured. As obvious from FIG. 16, the concentration of formaldehyde gas is reduced with progress of gas removal by the operation of the deodorizer. FIG. 16 shows that the relative concentration was reduced to 60 after 100 minutes from the start of operation of the deodorizer.

According to the seventh embodiment, the discharge mechanism 113, the photocatalyst modules 114 and the ozone decomposing catalyzer 115 are disposed in the blowing path 111 of the deodorizer. The photocatalyst modules 114 performs the photocatalytic action when subjected to the ultraviolet rays produced by the high-voltage discharge by the discharge mechanism 113, so that the ozone produced by means of the high-voltage discharge is decomposed by the catalyzer 115. Consequently, the odor component and injurious matter contained in the atmosphere are oxidized to be decomposed. Thus, decomposition and elimination of the odor component etc. present in the room are carried out using the ozone and ultraviolet rays both produced by the high-voltage discharge. Consequently, an adsorbent for deodorization need not be replaced by a new one, and drug need not be supplemented. Further, since the photocatalytic action and the ozone decomposing action are combined together, a wider range of odor component can be decomposed. Additionally, since the deodorizer 11 can produce the ultraviolet rays without using a fluorescent lamp, no special handling is required in the case of disposition of the deodorizer 11.

Furthermore, the discharge mechanism 113 and the photocatalyst modules 114 are detachably attached to the blowing path 111. Accordingly, when contaminants are adherent to the discharge electrode 117, counter electrodes 118, and photocatalyst modules 114, the discharge mechanism 113 is taken out of the body of the deodorizer so that the contaminants adherent to the these components are eliminated by water washing, for example. Further, the discharge mechanism 113 comprises the wire-shaped discharge electrodes 117 and the flat counter electrodes 118, and the discharge is directly executed between these electrodes. Consequently, a larger space for deodorization can be obtained as compared with a surface discharge system in which electric discharge is performed via an insulator. Further, since the high voltage of the negative polarity is applied across the discharge electrodes 117 and 118, a larger amount of ozone can be produced and accordingly, the deodorizing efficiency can be improved.

Further, the voltage applied to the discharge mechanism 113 is changed according to a volume of air supplied by the fan 116. Accordingly, the applied voltage is increased as the rotational speed of the fan 116 is decreased such that a flow rate of air is reduced. Consequently, a reduction in the deodorizing efficiency with the reduction in the flow rate of air can be compensated.

Furthermore, since each photocatalyst module 114 is disposed between the electrodes 117 and 118 of the discharge mechanism 113, the ultraviolet rays produced by the discharge mechanism 113 can efficiently be irradiated onto each photocatalyst module 114 and accordingly, the efficiency in the photocatalytic reaction can be improved. Further, the photocatalyst modules 114 are disposed at the upstream and downstream sides of the discharge mechanism 113. Consequently, the ultraviolet rays produced in the discharge mechanism 113 can be used further efficiently.

Additionally, each photocatalyst module 114 is formed by fixing titanium oxide to the surface of the base made from the porous ceramic. Consequently, the flow of air can be prevented from being blocked by each photocatalyst module 114 even when each module is disposed in the blowing path 111. Further, since an area of the base surface to which titanium oxide is fixed is rendered larger, the photocatalytic reaction can be performed with high efficiency even when an amount of titanium oxide which is an expensive material is reduced as much as possible, whereupon the injurious matter can efficiently be eliminated.

Figure 17:
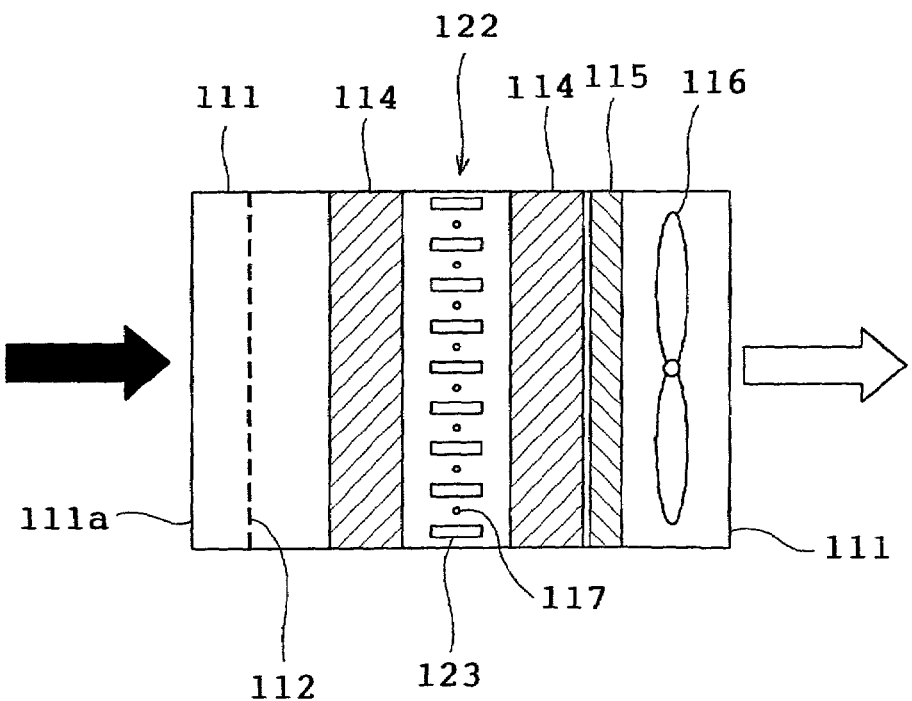
FIG. 17 is a view similar to FIG. 7, showing the deodorizer of an eighth embodiment in accordance with the invention.
Figure 18:
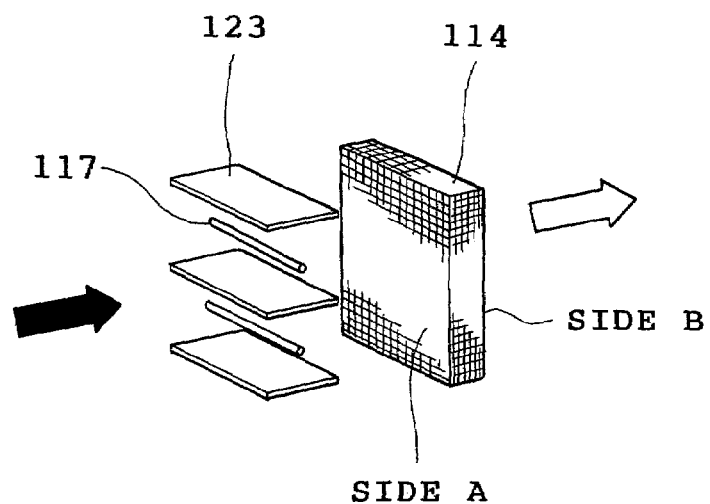
FIG. 18 is a perspective view of a part of the deodorizer shown in FIG. 17.

FIGS. 17 and 18 illustrate an eighth embodiment of the invention. In the eighth embodiment, a discharge mechanism (discharging means) 122 is provided instead of the mechanism 113. Each of a plurality of counter electrodes 123 whose number is equal to the number of discharge electrodes 117 plus one is formed into the shape of a rectangular plate. The discharge electrodes 117 and the counter electrodes 123 are disposed alternately so that flat faces of the counter electrodes 123 are parallel with the direction in which the air flows. The two photocatalyst modules 114 are disposed at the upstream and downstream sides of the discharge mechanism 122.

The discharge mechanism 122 is detachably attached to the blowing path 111 in the same manner as the mechanism 113 in the first embodiment. The photocatalyst module 114 discrete from the discharge mechanism 122 is also detachably attached to the path 111.

The operation of the deodorizer of the eighth embodiment is basically the same as that in the seventh embodiment. Furthermore, since the flat faces of the counter electrodes 123 are parallel with the direction in which the air is caused to flow, the flow of air through the blowing path 111 is prevented from being blocked.

Furthermore, in the eighth embodiment, when each photocatalyst module 114 having two sides A and B is attached to the blowing path 111, the side A confronting the mechanism 122 side and a side B opposed to the side A are changeable with each other. More specifically, contaminant is easy to adhere to the side A of each module 114 since the side A confronting the discharge mechanism 122 is subjected to an active photocatalytic reaction. Accordingly, when each module 114 is detached at a certain stage of adherence of contaminant and the sides A and B are changed with each other before water washing, the photocatalytic reaction can desirably be executed temporarily using the side B to which few contaminant is adherent.

According to the eighth embodiment, the side A confronting the mechanism 122 side and a side B opposed to the side A are changeable with each other when each photocatalyst module 114 is attached to the deodorizer 11B. Even when the photocatalytic reaction is reduced with a certain amount of contaminant adherent to the side A, the photocatalytic reaction can temporarily be activated as the result of change of the sides A and B with each other. Thus the photocatalyst module 114 can be used more effectively.

The invention should not be limited to the foregoing embodiments and may be modified as follows. In the first embodiment, the sides A and B of each photocatalyst module 74 can be changed with each other in the same manner as in the fourth embodiment. Further, the sides A and B of each photocatalyst module 114 in the seventh embodiment can also be changed with each other in the same manner as in the seventh embodiment.

Although two photocatalyst modules 74 are disposed at the upstream and downstream sides of the discharge mechanism 73, 82, 113 or 122 respectively in the foregoing embodiments, only one module may be disposed at either upstream or downstream side.

The voltage applied to the discharge electrodes 76 or 117 may have the positive polarity. The applied voltage should not be limited to the pulsed voltage and may be a steady AC or DC voltage. Further, the applied voltage may be set to be constant irrespective of a flow rate of the blowing path 71 or 111.

The control device 28 may interrupt the operation of the deodorizer 11 when the first or second door 7 or 14 is opened. As a result, the high-voltage discharge can be stopped when the user opens the door 7 or 14 to take food out of the refrigerator. The discharge mechanism may be of the flat surface type depending upon a set deodorizing capability. The counter electrode 77 or 118 may be meshed. The voltage applied to the discharge mechanism 73, 113 or 122 may be changed according to a set deodorizing capability as well as according to a supplied air volume.

The foregoing description and drawings are merely illustrative of the principles of the present invention and are not to be construed in a limiting sense. Various changes and modifications will become apparent to those of ordinary skill in the art. All such changes and modifications are seen to fall within the scope of the invention as defined by the appended claims.

We claim:

1. A refrigerator in which a deodorizer is provided in a cold air circulation path for deodorizing an atmosphere in the refrigerator, the refrigerator further comprising a heat exchanger having a cold air inlet, the deodorizer comprising:
    discharging means having a plurality of wire-shaped discharge electrodes disposed across the cold air circulation path and a flat counter electrode, the discharging means producing ozone and ultraviolet rays by means of high-voltage discharge, the counter electrode having a number of slits formed therethrough so that cold air for refrigeration flows through the slits, the slits being arranged so that the cold air flows therethrough across the counter electrode;
    a photocatalyst module provided between the discharge electrodes and the counter electrode for decomposing an odor component and injurious matter contained in the atmosphere by means of photocatalyst; and
    ozone decomposing means for decomposing the ozone produced by the discharging means, the ozone decomposing means being disposed at a downstream side of at least the discharging means and the photocatalyst module with respect to a direction in which the cold air flows and further in the cold air inlet of the heat exchanger.

2. A refrigerator according to claim 1, wherein two photocatalyst modules are disposed at upstream and downstream sides of the discharging means with respect to a direction in which the cold air flows, respectively.

3. A refrigerator according to claim 1, wherein the deodorizer includes a body and the photocatalyst module is attached to and detached from the body of the deodorizer.

4. A refrigerator according to claim 3, wherein the photocatalyst module has a first side confronting the discharging means and a second side located opposite the first side, and the first and second sides of the photocatalyst module are exchangeable when the photocatalyst module is attached to the body of the deodorizer so that the second side is confronting the discharging means.

5. A refrigerator according to claim 1, wherein the photocatalyst module includes a base made from a porous ceramic and a photocatalytic material fixed to a surface of the base.

6. A refrigerator according to claim 1, further comprising control means for controlling the deodorizer so that the discharging means discharges electricity when cold air is circulated in the refrigerator.

7. A refrigerator according to claim 1, wherein the deodorizer includes a fan for blowing against the discharging means and the photocatalyst module.

8. A refrigerator according to claim 1, wherein the deodorizer includes a body, and the discharging means includes two electrodes between which electric discharge is directly performed and is attached to and detached from the body of the deodorizer.

9. A refrigerator according to claim 1, wherein the discharging means includes a pair of electrodes across which a high voltage of a negative polarity is applied so that electric discharge is performed.

10. A refrigerator according to claim 1, further comprising voltage changing means for changing a discharge voltage of the discharging means.

11. A refrigerator according to claim 1, further comprising a door closing and opening an interior of the refrigerator and control means for controlling the deodorizer so that the discharging means interrupts electric discharge when the door is opened.

12. A refrigerator according to claim 1, wherein the discharging means includes a pair of electrodes and the photocatalyst module is disposed between the electrodes of the discharging means.

13. A refrigerator according to claim 1, further comprising a refrigerator body, wherein the deodorizer is attached to and detached from the refrigerator body.

14. A refrigerator according to claim 13, wherein at least the discharging means of the deodorizer is powered by a battery.

* * * * *